United States Patent [19]

Eriksen et al.

[11] Patent Number: 5,520,935

[45] Date of Patent: May 28, 1996

[54] METHOD FOR PRODUCTION OF PEA PROTEIN HYDROLYZATE

[75] Inventors: Svend Eriksen, Allerød; Per M. Nielsen, Hillerød, both of Denmark

[73] Assignee: Novo Nordisk A/S, Bagsvaerd, Denmark

[21] Appl. No.: 107,690

[22] PCT Filed: Mar. 6, 1992

[86] PCT No.: PCT/DK92/00069

§ 371 Date: Aug. 18, 1992

§ 102(e) Date: Aug. 18, 1992

[87] PCT Pub. No.: WO92/15697

PCT Pub. Date: Sep. 17, 1992

[30] Foreign Application Priority Data

Mar. 7, 1991 [EP] European Pat. Off. ............. 91610014

[51] Int. Cl.$^6$ ........................................ A23L 1/20
[52] U.S. Cl. ................. 426/46; 426/44; 426/49; 426/52; 426/656; 435/68.1
[58] Field of Search ................. 426/46, 49, 52, 426/63, 656, 478, 489, 490, 495, 629, 634, 44; 435/68.1; 530/370, 377, 379

[56] References Cited

U.S. PATENT DOCUMENTS

| 3,846,560 | 11/1974 | Hempenius et al. ................. 426/46 |
| 4,100,024 | 7/1978 | Adler-Nissen ................. 195/29 |
| 4,293,571 | 10/1981 | Olofsson et al. ................. 426/52 |
| 4,324,805 | 4/1982 | Olsen ................. 426/46 |
| 4,431,629 | 2/1984 | Olsen ................. 426/46 |
| 4,482,574 | 11/1984 | Lee ................. 426/7 |
| 4,677,065 | 6/1987 | Büchbjerg et al. ................. 435/68 |
| 4,959,350 | 9/1990 | Frokjaer et al. ................. 514/2 |

FOREIGN PATENT DOCUMENTS

| 0238946 | 9/1987 | European Pat. Off. . |
| 0325986 | 8/1989 | European Pat. Off. . |
| 214527 | 10/1984 | Germany . |
| 2216386 | 10/1989 | United Kingdom . |

OTHER PUBLICATIONS

Orbit Search Services, File WPAT, Accession No. 81-63585D/35, Anonymous.

*Primary Examiner*—Leslie Wong
*Attorney, Agent, or Firm*—Steve T. Zelson; Elias J. Lambiris

[57] ABSTRACT

The present invention relates to a pea protein hydrolyzate with very high purity and with organoleptic properties. The present invention also relates to a method for producing said pea protein hydrolyzate.

13 Claims, 2 Drawing Sheets

METHOD FOR PRODUCTION OF PEA PROTEIN HYDROLYZATE

CROSS-REFERENCE TO RELATED APPLICATIONS

This application is a continuation of PCT/DK92/00069 filed Jun. 3, 1992, which is incorporated herein by reference.

BACKGROUND OF THE INVENTION

1. Field of the Invention

The invention comprises a method for production of a pea protein hydrolyzate, a pea protein hydrolyzate and a use thereof.

2. Description of Related Art

Methods for production of vegetable protein hydrolyzates usually comprise a hydrolysis and a posttreatment in order to purify the vegetable protein hydrolyzate. An example of the hydrolysis appears from U.S. Pat. Nos. 4,324,805 and 4,100,024, and an example of the posttreatment appears from American Chemical Society Symposium No. 154, Synthetic Membranes, Vol. II, Hyper- and Ultrafiltration Uses.

Among dieticians on hospitals and homes for elderly people as well as for manufactureres of dietetic products, also intended for athletes, there is a need for special protein products. It is a desideratum that the protein should be fully soluble, also when heat treated, without raising the viscosity of the solution, and that the protein should exhibit a good nutritional value and that it will not cause organoleptic problems during formulation. Traditional protein products like pea isolate, soy isolate and gluten do not exhibit optimal properties; especially the solubility is a problem. By hydrolysis of the protein the solubility is improved. Hitherto the taste (bitterness) and/or processing costs have limited the availability of protein hydrolysates for generel applications. In selecting vegetable protein material for dietetic products meant for hospitalized people as the sole source of food special care shoudl be taken to diminish the content of phytate in the product since phytate reduces the bioavailability of certain minerals. Phytate is found in varying amounts in different vegetable raw materials, whereby pea protein exhibits a very low phytate content. This is reflected also in the hydrolysed protein making pea protein hydrolyzate a very convenient protein source for dietetic purposes in general, especially for critical patients.

Pea protein concentrate and isolate is an easily available protein source. Thus, it is the purpose of the invention to provide a pea protein hydrolyzate with good organoleptic properties and a method for production of the pea protein hydrolyzate with good organoleptic properties, which can be carried out with a relatively high yield.

SUMMARY OF THE INVENTION

Surprisingly, according to the invention it has been found that it is possible to provide a pea protein hydrolyzate of high purity and good organoleptic properties and that a certain combination of a non-pH-stat hydrolysis and an ultrafiltration provides a process for production of a well tasting and organoleptically acceptable product in high yield.

Thus, the method according to the invention for production of a pea protein hydrolyzate is characterized by the fact 1) that a pea protein product with at least 65% protein calculated as dry matter and water is mixed to a slurry with a protein content up to about 20%, preferably up to 12%, 2) that the mixture from step 1) by means of at least one protease is proteolytically hydrolyzed by means of a non-pH-stat method to a DH of between 15 and 35%, 3) that the hydrolysis is terminated by inactivation of the enzyme(s), and 4) that the mixture from step 3 is separated on an ultrafiltration unit with cut-off value above 5,000, the permeate constituting the protein hydrolyzate.

DETAILED DESCRIPTION OF THE INVENTION

Figure 1:
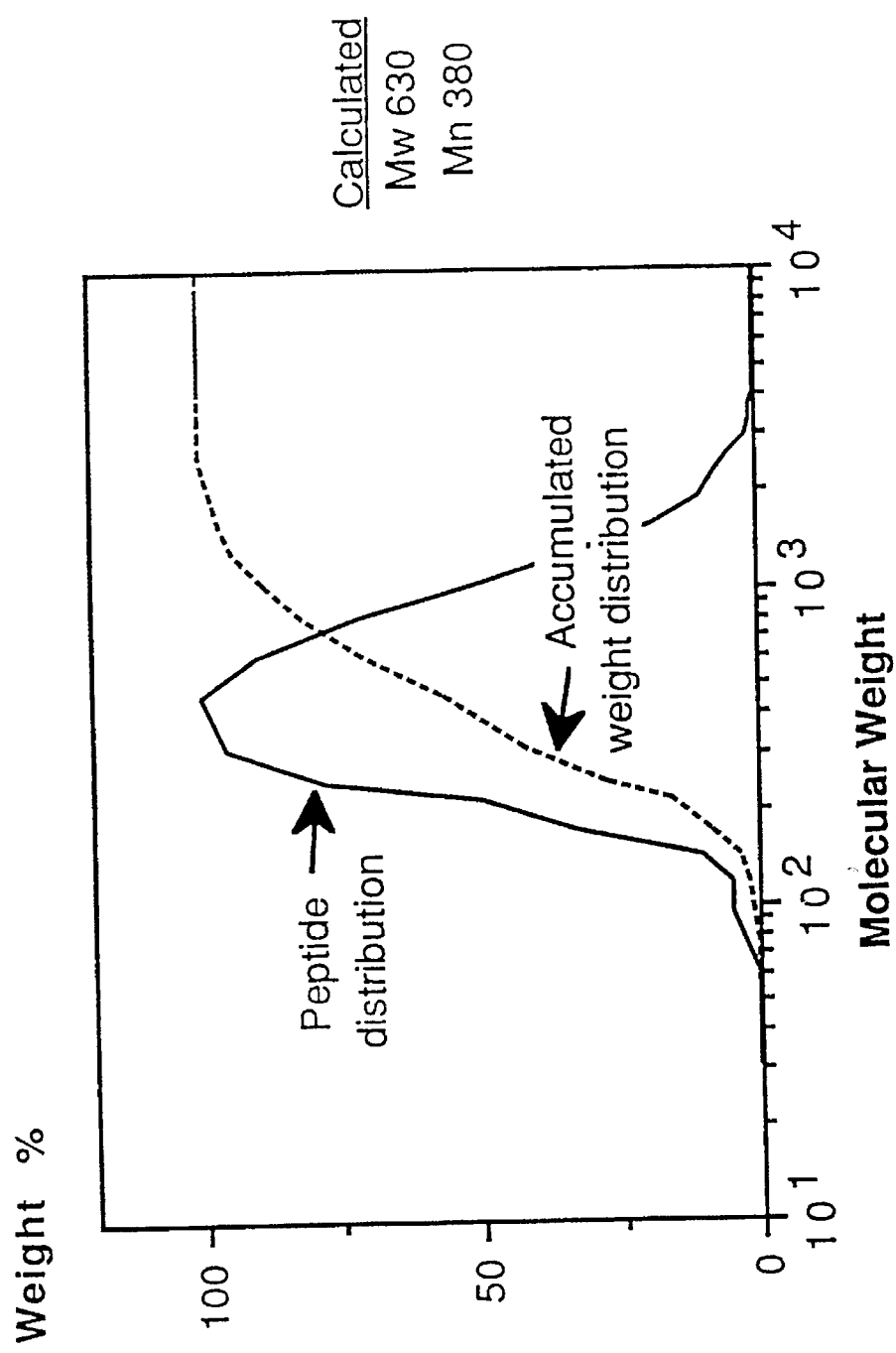
FIG. 1 shows the molecular weight distribution of a pea protein hydrolyzate according to the present invention.

It is to be understood that the pea protein product used as raw material in step 1 can be any pea protein product, provided that the protein content thereof is at least 65% calculated as dry matter, i.e. pea protein concentrates (with a protein content of above 70% calculated as dry matter), or pea protein isolates (with a protein content of above 90% calculated as dry matter).

In regard to step 2) it is preferred to conduct the hydrolysis at pH values and temperatures close to the optimum pH values and temperatures for the protease(s).

Also, it is to be understood that step 3) can be omitted, if the enzyme(s) is (are) retained in the retentate of step 4).

A preferred embodiment of the method according to the invention comprises that the pea protein product is a pea protein concentrate. Pea protein concentrates are commercially available standard products.

A preferred embodiment of the method according to the invention comprises that the pea protein product is a pea protein isolate. Pea protein isolates are commercially available standard products of high purity.

A preferred embodiment of the method according to the invention comprises that the slurry in step 1) has a protein content of 7–12%. In this manner the equipment is utilized optimally, and also, the viscosity is not too high for handling.

A preferred embodiment of the method according to the invention comprises that a heat treatment to a temperature above 60° C. is inserted between step 1 ) and step 2). In this manner the protein is effectively denatured, and thus, the subsequent hydrolysis will proceed rapidly. Also, the microbial stability during the hydrolysis, which can last for several hours, is secured effectively.

A preferred embodiment of the method according to the invnetion is characterized by the fact that the hydrolysis in step 2) is carried out to a DH of between 20 and 30, preferably between 25 and 30, and that an endoprotease or endoproteases are used as proteolytic enzyme(s). In this manner a pea protein hydrolyzate with a relatively low content of free amino acids and a relatively high degree of hydrolysis can be obtained. This makes the pea hydrolyzate especially well suited for dietetic purposes as short peptides (2–4 amino acids in chain length) are absorbed faster than free amino acids. Also the osmolality is kept relatively low in this pea protein hydrolyzate.

A preferred embodiment of the method according to the invention comprises that the hydrolysis in step 2) is carried out to a DH of between 20 and 30, preferably between 25 and 30, and that ALCALASE® (*B. licheniformis*) and/or NEUTRASE® (*B. subtilis*) is used as proteolytic enzyme(s). It is especially preferred to use ALCALASE® (with a high pH optimum) first, and then NEUTRASE® (with a lower pH optimum). This method is especially well suited to the non-pH-stat-method used in the method according to the invention.

A preferred embodiment of the method according to the invention comprises that the inactivation of the enzyme(s) (step 3)) is carried out by heat treatment. This inactivation is especially well suited in case the pH of the final pea protein hydrolyzate is supposed to be relatively high.

A preferred embodiment of the method according to the invention comprises that the inactivation of the enzyme(s) (step 3)) is carried out by acid treatment. This inactivation is especially well suited in case the pH of the final pea protein hydrolyzate is supposed to be relatively low.

A preferred embodiment of the method according to the invention comprises that the mixture at the end of step 3) is treated with activated carbon for more than 5 minutes at between 50° and 70° C. in an amount corresponding to between 1 and 5% carbon, calculated in relation to dry matter content. In this manner the color of the final pea protein hydrolyzate is improved, and also, the off-flavor is removed.

A preferred embodiment of the method according to the invention comprises that the permeate from step 4) is heated to between 130° and 140° C. and immediately thereafter flash cooled to around 75° C. and then cooled in a heat exchanger to between 50° and 60° C. In this manner the taste of the final pea protein hydrolyzate is improved, and also, the microbiological stability is secured.

A preferred embodiment of the method according to the invention comprises that after step 4) a concentration is carried out by nanofiltration at a temperature between 50° and 70° C. and/or evaporation, whereafter the retentate is collected as the pea protein hydrolyzate solution. By means of the nanofiltration a desalination can be carried out by proper selection of the membrane; besides nanofiltration is an inexpensive way for removal of water. Evaporation has the advantage of obtaining a high dry matter content in the concentrate before drying.

A preferred embodiment of the method according to the invention comprises that the pea protein hydrolyzate solution from step 4) is spray-dried to a water content below 6.5%. In this manner a stable product is obtained, both microbially and organoleptically.

Also, the invention comprises a pea protein hydrolyzate, which is characterized by the fact 1) that the content of protein (N*6.25), found as peptides and free amino acids, on a dry matter basis is >90% w/w, preferably >92% w/w, more preferably >94% w/w, and most preferably >95% w/w,
2) that the phytate content is <0.6% w/w,
3) that the content of amino acids is <10% w/w,
4) that 350<Mn<650, where Mn is the average molecular weight according to number,
5) that the content of peptides with $M_n$>5000 is <0.5% w/w,
6) that the organoleptic properties comprise no pea flavor and pea taste or a slight pea flavor and pea taste, and
7) that the degree of hydrolysis (DH) is between 20 and 35%

A preferred embodiment of the pea protein hydrolyzate according to the invention is characterized by the fact that the pea protein hydrolyzate is produced according to the method according to the invention. In this manner a pea protein hydrolyzate with high purity and excellent organoleptic properties is provided. A pea protein hydrolyzate with a purity of 94% and above is a novel product. All previously known pea protein hydrolyzates have had a much lesser purity.

Also, the invention comprises a use of the pea protein hydrolyzate according to the invention, as a nutrient, preferably as a nutritional additive to foods or beverages.

The pea protein hydrolyzate and the method for production thereof will be illustrated in the following examples.

EXAMPLE 1

Production of an Acidic Hydrolyzate from Pea Protein Isolate

Mixing 9.6 kg of pea protein isolate (P-PRO 2000 Nutrio/Danisco) containing 83.3% protein is mixed with water to a slurry with a protein content of 8.0%.

Heat Treatment

The mixture is heated to 85° C. and cooled again to 55° C. after a holding time of 1 minute.

Hydrolysis pH is adjusted to 8.5 with 4 N NaOH. The hydrolysis is carried out at 55° C. and is running for 18 hours. Hydrolysis is initiated by addition of ALCALASE® 2.4 L. The dosage is 2.0% of the amount of protein. pH is monitored and when pH have decreased to <7.0 NEUTRASE® 0.5 L is added to the mixture. The dosage is 1.0% of the amount of protein.

Inactivation of Enzyme

After 18 hours the hydrolysis is terminated by lowering the pH to 4.2 by means of 30% HCl.

Separation of Hydrolyzate

To the hydrolyzate activated carbon is added (PICATIF FGV120). The dosage is 3% of dry matter measured as Brix. The mixture is ultrafiltered by means of a PCI module mounted with FP100 membranes having a cut-off value of 100,000. The temperature during ultrafiltration is 55°–65° C. The volume of carbon containing mixture is concentrated to one third and subsequently diafiltered with two volumes of water. The ultrafiltration is terminated by means of a concentration step. The permeate is collected and the retentate discarded.

Flash

The permeate from the ultrafiltration is heated to 135° C. by steam injection and flash cooled within few seconds to approx. 75° C. followed by cooling to 55° C. for further processing.

Nanofiltration

The effluent from the flash process is concentrated and desalinated by nanofiltration to a dry matter content of approx. 25% (30° Brix). Nanofiltration equipment was AFC30 membranes from PCI Membrane Systems. The low osmolality of 180 mOsm/kg measured at 5.0% protein was obtained without diafiltration.

Sterilizing Filtration

To assure appropriate microbiological quality the concentrate from the nanofiltration is filtered at approx. 50° C. on SUPRA ESK® sheets rinsed with citric acid solution (50 l/m² at pH 4.2) and deionized water to neutral pH before steaming. 22 kg of filtrate containing 22.0% protein was obtained after this step.

Spray Drying

The filtrate is spray dried at an inlet temperature of 200° C. and an outlet temperature of 75° C. by means of a spray drying unit from Niro Atomizer with a capacity of approx. 2 l of evaporated water per hour.

| Characterization of end product | |
| --- | --- |
| Protein, % (N*6.25) | = 89.8% |
| Dry matter, % | = 94.0% |
| Ash, % | = 1.9% |
| Phytate, % | = 0.47% |
| Protein in dry matter, % | = 95.5% |
| Ash in dry matter, % | = 2.0% |
| Phytate | = 0.50% |
| Degree of Hydrolysis | = 27.6% |
| Osmolality in solution with 5.0% protein | = 180 mOsm/kg |
| pH in solution with 5.0% protein | = 4.03 |
| Color-absorbance at 450 nm in solution with 5.0% protein | = 0.065 |
| Mean molecular weight | = 380 |

Figure 2:
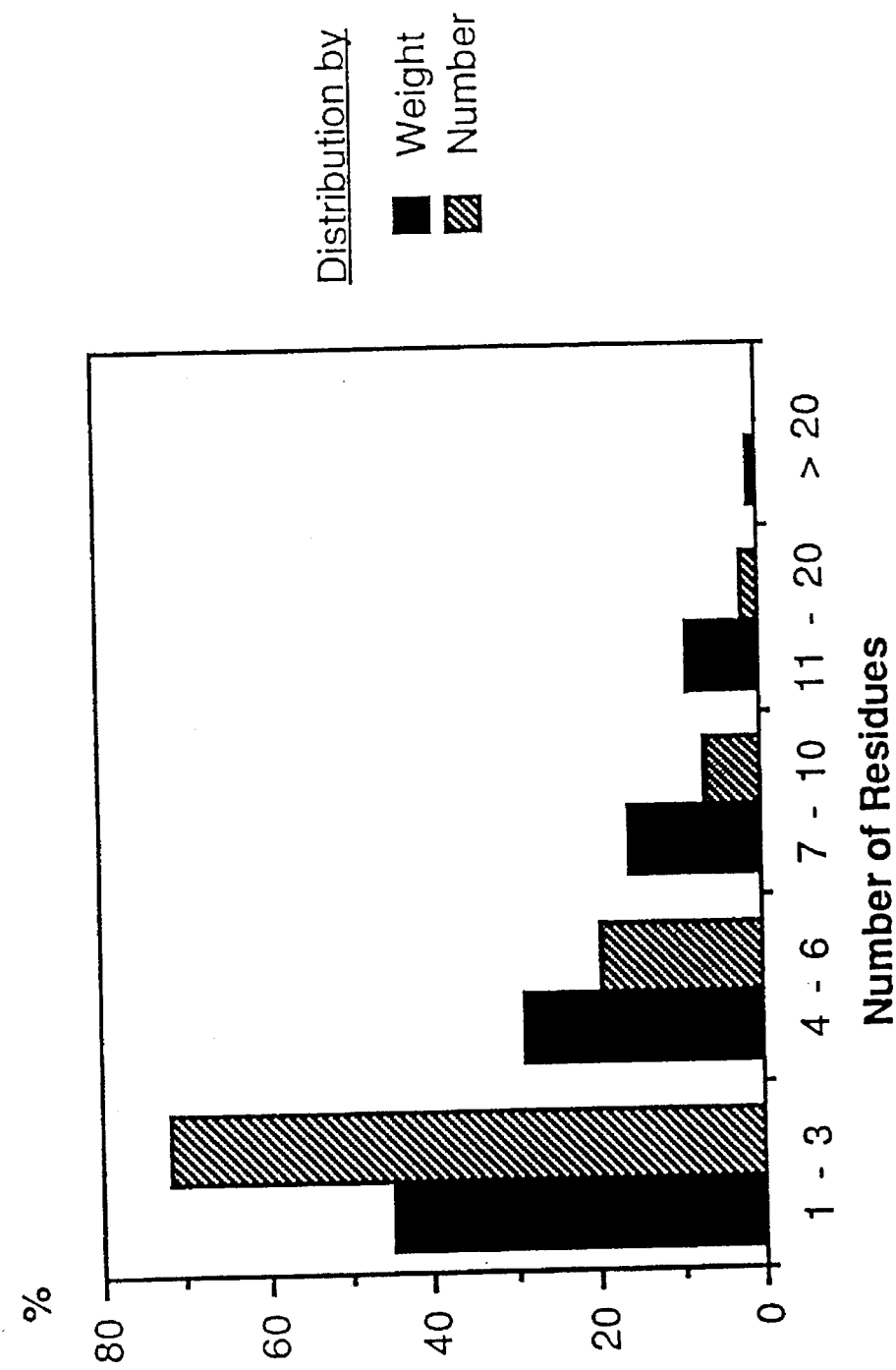
FIG. 2 shows the distribution of peptides of a pea protein hydrolyzate according to the present invention.

The molecular weight distribution appears from FIG. 1, and the distribution of peptides appear from FIG. 2.

EXAMPLE 2

Production of a Neutral Hydrolyzate from Pea Protein Isolate

Mixing 9.6 kg of pea protein isolate (P-PRO 2000® Nutrio/Danisco) containing 83.3% protein is mixed with water to a slurry with a protein content of 8.0%.

Heat Treatment

The mixture is heated to 85° C. and cooled again to 55° C. after a holding time of 1 minute.

Hydrolysis pH is adjusted to 8.5 with 4 N NaOH. The hydrolysis is carried out at 55° C. and is running for 18 hours. Hydrolysis is initiated by addition of ALCALASE® 2.4L. The dosage is 2.0% of the amount of protein. pH is monitored and when pH have decreased to <7.0 NEUTRASE® 0.5L is added to the mixture. The dosage is 1.0% of the amount of protein.

Inactivation of Enzyme

After 18 hours the hydrolysis is terminated by heating to 85° C., by holding this temperature for 3 minutes, and by cooling to 55° C.

Separation of Hydrolyzate

To the hydrolyzate activated carbon is added (PICATIF FGV120®). The dosage is 3% of dry matter measured as °Brix. The mixture is ultrafiltered by means of a PCl module mounted with FP100 membranes having a cut-off value of 100,000. The temperature during ultrafiltration is 55°–65° C. The volume of carbon containing mixture is concentrated to one third and subsequently diafiltered with two volumes of water. The ultrafiltration is terminated by means of a concentration step. The permeate is collected and the retentate discarded.

Flash

The permeate from the ultrafiltration is heated to 135° C. by steam injection and flash cooled within few seconds to approx. 75° C. followed by cooling to 55° C. for further processing.

Nanofiltration

The effluent from the flash process is concentrated and desalinated by nanofiltration to a dry matter content of approx. 25% (30° Brix). Nanofiltration equipment was AFC30 membranes from PCl Membrane Systems. The low osmolality of 161 mOsm/kg measured at 7.5° Brix was was obtained by diafiltration of 176 l of concentrate with 80 l of water. The diafiltration was carried out after concentration of the 176 l to 28 l.

Sterilizing Filtration

To assure appropriate microbiological quality the concentrate from the nanofiltration is filtered at approx. 50° C. on SUPRA EKS ® sheets rinsed with citric acid solution (50 l/m² at pH 4.2) and deionized water to neutral pH before steaming.

Spray drying

The filtrate is spray dried at an inlet temperature of 200° C. and an outlet temperature of 75° C. by means of a spray drying unit from Niro Atomizer with a capacity of approx. 2 l of evaporated water per hour.

EXAMPLE 3

Production of a Neutral Hydrolyzate from Pea Protein Isolate

The effluent from the flash in Example 3 is collected for concentration without desalination, i.e. by evaporation; it is concentrated in a rotary vacuum evaporator to a dry matter content of approx. 25%.

The concentrate is spray dried at an inlet temperature of 200° C. and an outlet temperature of 75° C. by means of a spray drying unit from Niro Atomizer with a capacity of approx. 2 l of evaporated water per hour.

| Application of end product | | | |
| --- | --- | --- | --- |
| Dietary drinks with pH <4.5 | + | − | − |
| Protein supplements, soft drinks drinks with pH <4.5 | + | − | − |
| Protein fortification of soups, fond etc | − | + | + |
| Dietary drinks at neutral pH | − | + | + |

EXAMPLE 4

Production of a Neutral Hydrolyzate from Pea Protein Isolate 9.53 kg of pea protein isolate was processed by use of same process parameters as in Example 2. The only difference was the pea protein that was obtained from Cosuca, B-4350 Morealie, Belgium and that the nanofiltration was carried out without diafiltration.

It appears from the examples that it is possible to produce both an acidic and a neutral pea protein hydrolyzate of very high purity by means of the method according to the invention. In this context high purity means high protein content, calculated as dry matter, and correspondingly low content of antinutritional factors, e.g. phytate. This is surprising, since this has not been obtained with any of the other vegetable protein products examined by applicants.

In order to generate a better survey of all 4 examples reference is made to the below indicated table.

|  | Ex. 1 | Ex. 2 | Ex. 3 | Ex. 4 |
|---|---|---|---|---|
| Parameters of processing | | | | |
| DH in hydrolysis, % | 25.3 | 25.8 | 25.8 | 23.1 |
| Increase in osmolality during hydrolysis mOsm/kg | 183 | 182 | 182 | 153 |
| Properties of end product | | | | |
| DH of product, % | 27.6 | 28.5 | 30.9 | 26.7 |
| pH of product (in solution with 5% protein) | 4.03 | 6.53 | 6.98 | 6.64 |
| Osmolality of product, mOsm/kg (in solution with 5% protein) | 180 | 150 | 172 | 138 |
| Protein content, % (N*6.25) | 89.8 | 91.2 | 89.0 | 94.4 |
| Dry matter, % | 94.0 | 95.3 | 94.5 | 96.0 |
| Protein in d.m., % | 95.5 | 95.7 | 94.2 | 98.3 |
| Application of end product | | | | |
| Dietary drinks with pH <4.5 | + | − | − | − |
| Protein supplements, soft drinks drinks with pH <4.5 | + | − | − | − |
| Protein fortification of soups, fonds etc | − | + | + | + |
| Dietary drinks at neutral pH | − | + | + | + |

EXAMPLE 5

Application of Acidic Pea Protein Hydrolyzate as Nutrient in a Soft Drink

As an appliction example acidic pea protein hydrolyzate product from Example 1 was incorporated in a recipe for an apple flavoured soft drink:

| Water | 83.7% |
|---|---|
| Sucrose | 10.0% |
| Pea protein hydrolyzate | 5.57% |
| Citric acid | 0.3% |
| Malic acid | 0.2% |
| Ascorbic acid | 0.1% |
| Na-benzoate | 0.02% |
| Aspartame | 0.025% |
| Apple flavour E8396L (Fries & Fries) | 0.03% |

Evaluation of the drink showed a palatable drink with neither off flavour nor bitterness.

EXAMPLE 6

Application of Neutral Pea Hydrolyzate as Nutrient in Soup

As another application sample neutral pea protein hydrolysate product from Example 4 was dissoved in warm soup (drinking bouillon from Knorr prepared from the recipe on the package). Concentration of pea protein (N×6.25) in the soup was 3.5%. Taste evaluation of the soup showed that the protein enriched soup was only very slightly different from the soup without protein and that neither off flavour nor bitterness was detected.

We claim:

1. A method for producing a pea protein hydrolyzate, comprising (a) mixing water and a pea protein product with at least 65% protein calculated as dry matter to form a slurry with a protein content up to about 20%;

(b) hydrolyzing said slurry by one or more proteases using a non-pH-stat method to form a hydrolyzed mixture which has a degree of hydrolysis of between 15 and 35%;

(c) inactivating said one or more proteases; and (d) subjecting the hydrolyzed mixture to an ultrafiltration unit with a cut-off value above 5,000 to form a permeate comprising the pea protein hydrolyzate.

2. The method according to claim 1, wherein the pea protein product is a pea protein concentrate.

3. The method according to claim 1, wherein the pea protein product is a pea protein isolate.

4. The method according to claim 1, wherein the slurry has a protein content of 7–12%.

5. The method according to claim 1, further comprising heating the slurry to a temperature above 60° C. prior to hydrolyzing the slurry.

6. The method according to claim 1, wherein the hydrolyzed mixture has a degree of hydrolysis of between 20 and 30% and the one or more proteases are endoproteases.

7. The method according to claim 1, wherein the hydrolyzed mixture has a degree of hydrolysis of between 20 and 30% and the one or more proteases are derived from *B. licheniformis* or *B. subtilis*.

8. The method according to claim 1, wherein the one or more proteases are inactivated by heat treatment.

9. The method according to claim 1, wherein the one or more proteases are inactivated by acid treatment.

10. The method according to claim 1, further comprising, after inactivating the one or more proteases and prior to subjecting the hydrolyzed mixture to the ultrafiltration unit, treating the hydrolyzed mixture with activated carbon for more than 5 minutes at between 50° and 70° C. in an amount between 1 and 5% carbon, calculated in relation to dry matter content.

11. The method according to claim 1, further comprising heating the permeate to a temperature between 130° and 140° C. and immediately thereafter flash cooling the heated permeate to around 75° C. and then cooling to between 50° and 60° C. in a heat exchanger.

12. The method according to claim 1, further comprising concentrating the permeate by nanofiltration at a temperature between 50° and 70° C. to form a retentate comprising the protein hydrolyzate solution or by evaporation.

13. The method according to claim 1, further comprising spray drying the permeate to a water content below 6.5%.

\* \* \* \* \*